US00PP37812P2

(12) United States Plant Patent
van Swieten

(10) Patent No.: US PP37,812 P2
(45) Date of Patent: Oct. 20, 2026

(54) ***PHALAENOPSIS* PLANT NAMED 'PHA484007'**

(50) Latin Name: *Phalaenopsis hybrida*
Varietal Denomination: PHA484007

(71) Applicant: ANTHURA B.V., Bleiswijk (NL)

(72) Inventor: Martinus Nicolaas Gerardus van Swieten, Wageningen (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/559,946

(22) Filed: Mar. 7, 2026

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phalaenopsis* plant named 'PHA484007', characterized by its upright plant habit; moderately vigorous growth habit; strong flowering stems; freely flowering habit with typically two inflorescences developing per plant, each inflorescence with numerous flowers; medium-sized dark purplish red-colored flowers with purplish red-colored labella; and good postproduction longevity.

2 Drawing Sheets

Figure 1:
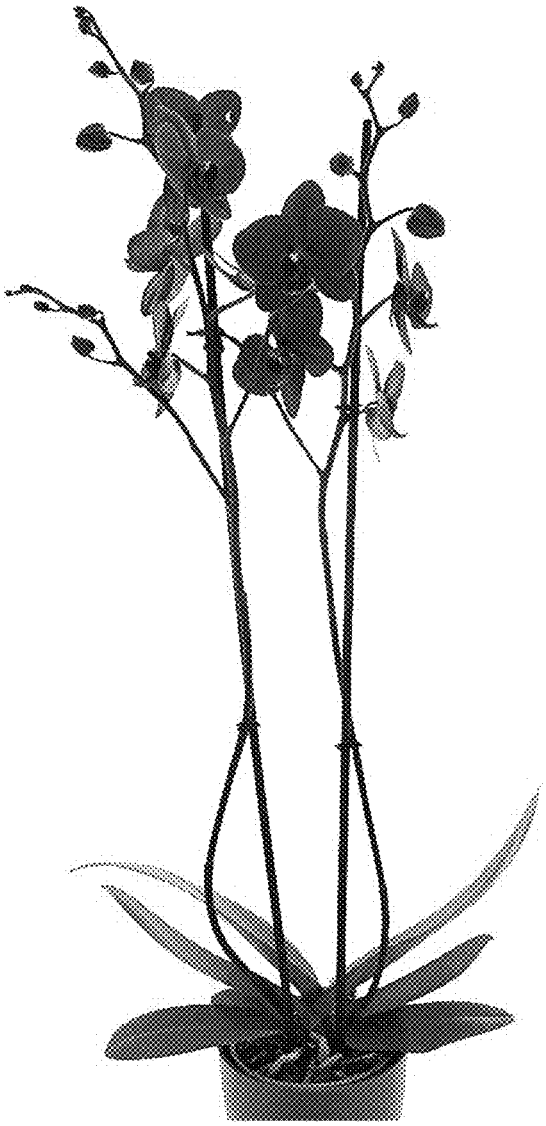

Botanical designation: *Phalaenopsis hybrida.*
Cultivar denomination: 'PHA484007'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B.V. of Bleiswijk, The Netherlands on Apr. 18, 2025, application number 2025/0840. Foreign priority is not claimed to this application.

BACKGROUND OF THE INVENTION

The present invention relates to a new and distinct cultivar of *Phalaenopsis* plant, botanically known as *Phalaenopsis hybrida,* commonly referred to as a *Phalaenopsis* or Moth Orchid and hereinafter referred to by the name 'PHA484007'.

The new *Phalaenopsis* plant is a product of a planned breeding program conducted by the Inventor in Bleiswijk, The Netherlands. The objective of the breeding program is to develop new freely flowering *Phalaenopsis* plants with dark purplish red-colored flowers.

The new *Phalaenopsis* plant originated from a cross-pollination in August 2017 in Bleiswijk, The Netherlands of a proprietary breeding selection of *Phalaenopsis hybrida* identified as code number 14-60514-11, not patented, as the female, or seed, parent with a proprietary breeding selection of *Phalaenopsis hybrida* identified as code number 00001-3768, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in June 2020.

Asexual reproduction of the new *Phalaenopsis* plant by in vitro meristem propagation in a controlled environment in Bleiswijk, The Netherlands since June 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA484007'. These characteristics in combination distinguish 'PHA484007' as a new and distinct *Phalaenopsis* plant:

1. Upright plant habit.
2. Moderately vigorous growth habit.
3. Strong flowering stems.
4. Freely flowering habit with typically two inflorescences developing per plant, each inflorescence with numerous flowers.
5. Medium-sized dark purplish red-colored flowers with purplish red-colored labella.
6. Good postproduction longevity.

Plants of the new *Phalaenopsis* can be compared to plants of the female parent selection. Plants of the new *Phalaenopsis* differ primarily from plants of the female parent selection in the following characteristics:

1. Flowers of plants of the new *Phalaenopsis* are not as broad as flowers of plants of the female parent selection.

2. Flower petals of plants of the new *Phalaenopsis* are darker purplish red in color than flower petals of plants of the female parent selection.

Plants of the new *Phalaenopsis* can be compared to plants of the male parent selection. Plants of the new *Phalaenopsis* differ primarily from plants of the male parent selection in the following characteristics:

1. Leaves of plants of the new *Phalaenopsis* have acute apices whereas leaves of plants of the male parent selection have obtuse apices.
2. Flowers of plants of the new *Phalaenopsis* are broader than flowers of plants of the male parent selection.
3. Flower petals of plants of the new *Phalaenopsis* are dark purplish red in color whereas flower petals of plants of the male parent selection are red in color.

Plants of the new *Phalaenopsis* can be compared to plants of *Phalaenopsis hybrida* 'PHA1904894', disclosed in U.S. Plant Pat. No. 33,554. In side-by-side comparisons, plants of the new *Phalaenopsis* differ primarily from plants of 'PHA1904894' in the following characteristics:

1. Leaves of plants of the new *Phalaenopsis* are semi-erect to horizontal whereas leaves of plants of 'PHA1904894' are horizontal.
2. Leaves of plants of the new *Phalaenopsis* have acute apices whereas leaves of plants of 'PHA1904894' have obtuse apices.
3. Central lobes of the labella of plants of the new *Phalaenopsis* are ovate in shape whereas central lobes of the labella of plants of 'PHA1904894' are trullate to rhombic in shape.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA484007' grown in a container.

Figure 2:
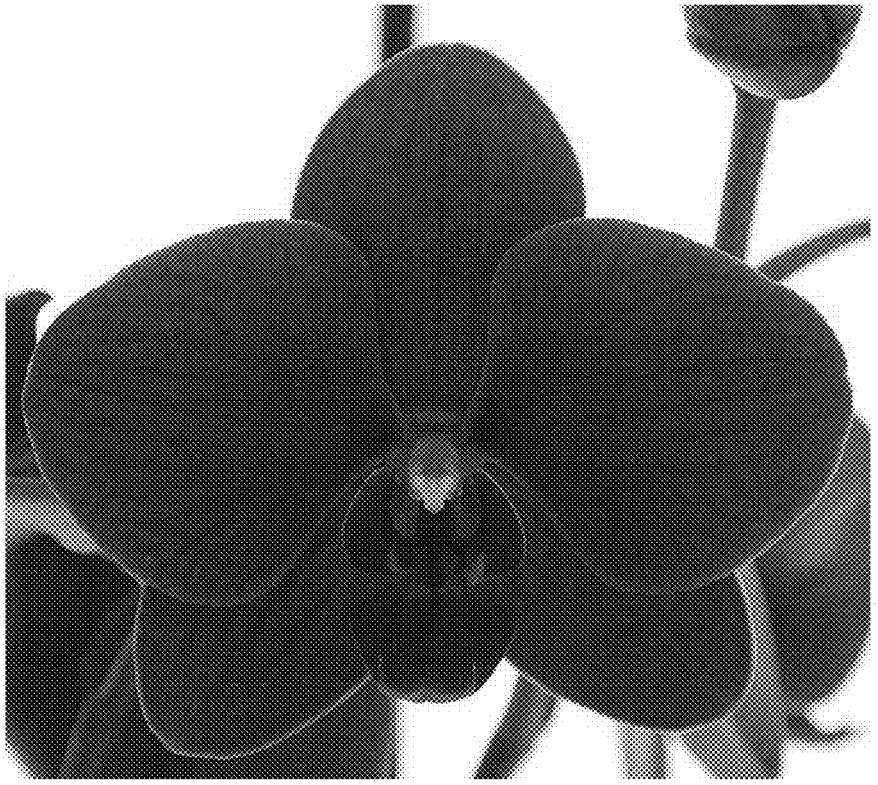

The photograph on the second sheet (FIG. 2) is a close-up view of a typical flower of 'PHA484007'.

DETAILED BOTANICAL DESCRIPTION

The aforementioned photographs and following observations and measurements describe plants grown during the early autumn in 12-cm containers in a glass-covered greenhouse in Bleiswijk, The Netherlands and grown under cultural practices typically used in commercial *Phalaenopsis* production. Plants were 18 months old when the photographs and description were taken. During the first 14 months of production of the plants, day and night temperatures averaged 28.5° C., and during the last four months of production of the plants, day and night temperatures averaged 20° C. Throughout the production of the plants, light levels ranged from 100μmol to 180μmol. In the following description, color references are made to The Royal Horticultural Society Colour Chart, 2015 Edition, except where general terms of ordinary dictionary significance are used.

Botanical classification: *Phalaenopsis hybrida* 'PHA484007'.

Parentage:

*Female, or seed, parent*.—Proprietary breeding selection of *Phalaenopsis hybrida* identified as code number 14-60514-11, not patented.

*Male, or pollen, parent*.—Proprietary breeding selection of *Phalaenopsis hybrida* identified as code number 00001-3768, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically light green in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit; typically two inflorescences developing per plant, each inflorescence with numerous flowers; monopodial; moderately vigorous growth habit and moderate growth rate.

*Plant height, substrate level to top of foliar plane*.—About 15.6 cm.

*Plant height, substrate level to top of floral plane*.—About 66 cm.

*Plant diameter or spread*.—About 27.1 cm.

Leaf description:

*Arrangement and quantity*.—Distichous, simple; sessile; about six to seven fully-developed leaves per plant.

*Length*.—About 19.8 cm.

*Width*.—About 8.2 cm.

*Aspect*.—Semi-erect to horizontal.

*Shape*.—Obovate to elliptic-obovate; slightly carinate.

*Apex*.—Unequal acute to broadly and unequal acute.

*Base*.—Sheathing. Sheath length: About 1.8 cm. Sheath width: About 1.3 cm. Sheath color: Close to 144B; at the margins and apex, tinged with close to N186C.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to NN137B. Developing leaves, lower surface: Close to a blend of 146B and 147B. Fully expanded leaves, upper surface: Close to NN137A; narrow marginal edges, close to 137B; venation, close to a blend of 139A and 147A. Fully expanded leaves, lower surface: Close to 146B; venation, close to 137B.

Inflorescence description:

*Appearance and flowering habit*.—Showy zygomorphic flowers arranged on axillary simple or branched racemes; typically two inflorescences develop per plant; each inflorescence with about 14 flowers; flowers face outwardly on upright to outwardly arching inflorescences supported by upright peduncles; flowers with three petals, two lateral petals and one center petal transformed into a labellum and three sepals.

*Fragrance*.—None detected.

*Time to flower*.—Plants begin flowering about five months after planting; plants flower naturally during the winter into the spring.

*Flower longevity*.—Long flowering period, individual inflorescences last for about 21 weeks on the plant; flowers not persistent.

*Inflorescence length* (*lowermost flower to inflorescence apex*).—About 28.1 cm.

*Inflorescence width*.—About 19.9 cm.

*Flower buds*.—Height: About 1.8 cm. Diameter: About 1.2 cm by 1.4 cm. Shape: Broadly ovate. Color: Close to N77B tinged with close to 152D; venation, close to 187A.

*Flower size*.—About 8 cm (vertical) by 9 cm (horizontal).

*Flower depth*.—About 2.8 cm.

*Petals, quantity and arrangement*.—Three, two lateral petals and one center petal transformed into a labellum.

*Lateral petals*.—Length: About 4.3 cm. Width: About 4.4 cm. Shape: Broadly ovate to broadly deltoid-ovate. Apex: Rounded to shallowly retuse. Margin: Entire; not undulate. Texture and luster, upper surface: Smooth, glabrous; moderately velvety; matte. Texture and luster, lower surface: Smooth, glabrous; slightly velvety; matte. Color: When opening, upper surface: Close to N79C; venation, close to N79B. When opening, lower surface: Close to N79D; center and towards the base, tinged with close to N77B and 186C; venation, close to N79C. Fully opened, upper surface: Close to N79C; venation, close to N78A; colors do not change with subsequent development. Fully opened, lower surface: Close to a blend of N79C and N79D; center and towards the base, close to 84B and 84C; venation, close to 72B; colors do not change with subsequent development.

*Labella*.—Appearance: Three-parted with two lateral lobes and a central lobe; overall shape, broadly cordate to reniform. Length, lateral lobes: About 1.7 cm. Width, lateral lobes: About 9 mm. Length, central lobe: About 2 cm. Width, central lobe: About 9 mm to 17 mm. Length, cirrhose tips: About 5 mm. Shape, lateral lobes: Obovate. Shape, central lobe: Ovate with a slightly elongated apex. Apex, lateral lobes: Obtuse. Apex, central lobe: Cleft with two cirrhose apices, pointing upwards and backwards. Margins, lateral and central lobes: Entire. Texture and luster, lateral and central lobes, upper and lower surfaces: Smooth, glabrous; moderately velvety; matte. Callosities: Located at the base of the labellum and attachment point of the lateral petals; about 4 mm in length, about 4.5 mm in width and about 3 mm in height. Color: When opening, upper surface: Lateral lobes: Close to 187B; towards the apex, close to N79C; at the base, close to 155B. Central lobe: Close to a blend of N79C and N186D; towards the base, close to 184B; at the base, close to 180A and 180B. Callosities: Close to 187C blotched with close to 22A; edges, close to 2C. When opening, lower surface: Lateral lobes: Close to N79B; towards the apex, close to N79D; at the base, close to N155A. Central lobe: Close to N79B; towards the base, close to NN78B and 197D; at the base, close to 197D. Fully opened, upper surface: Lateral lobes: Close to 187A; towards the apex, close to N79B; at the base, tinged with close to 22A and 22B. Central lobe: Close to N186D; towards the base, tinged with close to 180A; at the base, close to 180A and 180B. Callosities: Close to 187B and 187C blotched with close to 22A. Fully opened, lower surface: Lateral lobes: Close to N79A; towards the apex, close to N79C; at the base, close to 155A. Central lobe: Close to N79B; towards the base, close to NN78B and 84B; at the base, close to 187D.

*Sepals*.—Quantity and arrangement: Three, one upper dorsal sepal and two lower lateral sepals. Length, dorsal sepal: About 4.4 cm. Width, dorsal sepal: About 3.5 cm. Length, lateral sepals: About 4.3 cm. Width, lateral sepals: About 3 cm. Shape, dorsal sepal: Broadly ovate to close to broadly elliptic. Shape, lateral sepals: Broadly ovate. Apex, dorsal sepal: Obtuse to shallowly retuse. Apex, lateral sepals: Broadly acute to narrowly obtuse. Base, dorsal and lateral sepals: Cuneate. Margins, dorsal and lateral sepals: Entire; not undulate. Texture and luster, dorsal and lateral sepals, upper surface: Smooth, glabrous; moderately velvety; moderately glossy. Texture and luster, dorsal and lateral sepals, lower surface: Smooth, glabrous; slightly velvety; slightly glossy. Color, dorsal sepal: When opening, upper surface: Close to N79C with fine dots, close to 76B; venation, close to N79B. When opening, lower surface: Close to 152D; towards the margins, close to N77B; venation, close to N77A. Fully opened, upper surface: Close to N79C with fine dots, close to 76B; venation, close to NN78A. Fully opened, lower surface: Close to a blend of 84B and 197D; towards the margins, close to N78B; venation, close to N78A. Color, lateral sepals: When opening, upper surface: Close to N186D with fine dots, close to 76B; venation, close to 187A. When opening, lower surface: Close to 176B; at the margins, tinged with close to N77B; venation, close to N79B. Fully opened, upper surface: Close to N79C; proximally, close to a blend of N79B and N79C with fine dots, close to 76B; venation, close to N79B. Fully opened, lower surface: Close to a blend of 84B and 197D; at the margins, tinged with close to N79C; venation, close to N79B.

*Peduncles*.—Length: About 63.9 cm. Diameter: About 5.5 mm. Strength: Sturdy. Aspect: Upright to outwardly arching. Texture and luster: Smooth, glabrous; matte. Color: Close to N189A densely covered with fine dots, close to 147D.

*Pedicels*.—Length: About 4.8 cm. Diameter: About 3.5 mm. Strength: Moderately strong. Aspect: About 50° from peduncle axis. Texture and luster: Smooth, glabrous; matte. Color: Close to N148A; proximal end, close to 148A tinged with close to N77A; distal end, close to N78D.

*Reproductive organs*.—Androecium: Column length: About 9 mm. Column width: About 6 mm. Column color: Close to NN78B; towards the sides, close to N78B; at the apex, close to 76B. Pollinia quantity: Two. Pollinia diameter (per two pollinia): About 2.5 mm. Pollinia color: Close to 23A. Gynoecium: Stigma length: About 4 mm. Stigma width: About 4 mm. Stigma shape: Reniform. Stigma color: Close to N75C. Ovary length: About 1.6 cm. Ovary diameter: About 1 mm. Ovary color: Close to 149B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA484007' as herein illustrated and described.

* * * * *